(12) United States Patent
Tsubota et al.

(10) Patent No.: US 6,852,687 B2
(45) Date of Patent: Feb. 8, 2005

(54) METHOD FOR INHIBITING APOPTOSIS

(75) Inventors: Kazuo Tsubota, 5-26-7, Nishifuna, Funabashi-shi, Chiba-ken (JP), 273-0031; Akihiro Higuchi, Kashiwa (JP)

(73) Assignees: Kazuo Tsubota, Chiba-ken (JP); Sucampo AG, Zug (CH)

( * ) Notice: Subject to any disclaimer, the term of this patent is extended or adjusted under 35 U.S.C. 154(b) by 94 days.

(21) Appl. No.: 10/132,567

(22) Filed: Apr. 26, 2002

(65) Prior Publication Data

US 2002/0187927 A1 Dec. 12, 2002

(30) Foreign Application Priority Data

Apr. 26, 2001 (JP) ............................ 2001-129472
Oct. 19, 2001 (JP) ............................ 2001-322051

(51) Int. Cl.$^7$ .............................................. A61K 38/00
(52) U.S. Cl. ........................................................ 514/2
(58) Field of Search ............................................. 514/2

(56) References Cited

U.S. PATENT DOCUMENTS

| | | | | |
|---|---|---|---|---|
| 5,942,487 A | * | 8/1999 | Ogawa et al. ............... | 514/2 |
| 6,043,213 A | | 3/2000 | Tsubota | |
| 6,087,395 A | | 7/2000 | Watanabe et al. | |
| 2001/0036939 A1 | * | 11/2001 | Fliss .......................... | 514/184 |
| 2002/0007217 A1 | * | 1/2002 | Jacob et al. ................ | 623/5.16 |

OTHER PUBLICATIONS

Zoellner et al. Inhibition of microvascular endothelial apoptosis in tissue explants by serum albumin. Microvasc. Res. Mar. 1999, 57(2): 162–73.*

Zoelnner et al. Serum albumin is a specific inhibitor of apoptosis in human endothelial cells. J Cell Sci. Oct. 1996; 109 ( Pt 10):2571–80.*

Jose Iglesias et al.; "Albumin Is A Major Serum Survival Factor For Renal Tubular Cells And Macrophages Through Scavenging Of ROS"; The American Physiological Society; 1999; pp. F711–F722.

Hans Zoellner et al.; "Inhibition of Mircovascular Endothelial Apoptosis In Tissue Explants By Serum Albumin"; Microvascular Research 57; 1999; pp. 162–173.

Shih–Lan Hsu et al.; "Retinoic Acid–Induced Apoptosis Is Prevented By Serum Albumin And Enhanced By Lipiodol In Human Hepatoma Hep3B Cells"; Cancer Letters 129; 1998: pp. 205–214.

Yiqun Wang et al.; "BFGF Suppresses Serum–Deprivation–Induced Apoptosis In A Human Lens Epithelial Cell Line"; Experimental Cell Research 249; 1999; pp. 123–130.

Anita Singh et al.; "Synergistic Interaction Of Growth Factors And Albumin In Regulating Estradiol Synthesis In Breast Cancer Cells"; Molecular And Cellular Endocrinology 85; 1992; pp. 165–173.

Goran Boskovic et al.; "Local Control Of $\alpha$ 1–Proteinase Inhibitor Levels: Regulation Of $\alpha$ 1–Proteinase Inhibitor In The Human Cornea By Growth Factors And Cytokines"; Biochimica et Biophysica Acta 1103; pp. 37–46.

Podskochy et al., "Apoptosis in UV–exposed Rabbit Corneas", 2000 Lippincott Williams & Wilkins Inc., Philadelphia, pp. 99–103, Cornea 19(1), 2000.

Heiligenhaus et al., "Apoptosis in human non–necrotizing stromal herpes simplex keratitis", Klin Monatsbl Augenheilkd 2000 Sep.; 217(3): 178–82.

Aoyama–Hayashi et al., "PGE$_1$ inhibited daunorubicin–induced apoptosis of human leukemia cell line", Japanese Journal of Inflammation, vol. 18, No. 5 Sep. 1998, pp. 369–376.

* cited by examiner

*Primary Examiner*—Christopher R. Tate
*Assistant Examiner*—Maury Audet
(74) *Attorney, Agent, or Firm*—Sughrue Mion, PLLC

(57) ABSTRACT

The present invention relates to a method for treating a subject having a condition or disease involving apoptosis, which comprises administering an effective amount of albumin to the subject. The apoptosis inhibiting activity of albumin can be increased by administering a cell growth factor such as epidermal growth factor, transforming growth factor, fibroblast growth factor, hepatocyte growth factor, insulin-like growth factor, platelet-derived growth factor and nerve growth factor and/or vitamin A together with albumin.

16 Claims, 5 Drawing Sheets

Fig. 1 Caspase-3 activity

**p<0.01: Comparison with the control group (Tukey-Kramer test)
p<0.01: Comparison with the group receiving albumin (Tukey-Kramer test)

Fig. 2 Caspase-3 activity

**p<0.01: Comparison with the control group (Tukey-Kramer test)
p<0.01: Comparison with the group receiving albumin (Tukey-Kramer test)

Fig 3 Caspase-3 activity

$p<0.01$: Comparison with the group receiving albumin(Tukey-Kramer test)

Fig.4 Caspase-3 Acyivity p<0.01: Comparison with the group receiving albumin(Tukey-Kramer test)

Fig.5 Caspase-3 Activity p<0.01: Comparison with the group receiving albumin(Tukey-Kramer test)

METHOD FOR INHIBITING APOPTOSIS

BACKGROUND OF THE INVENTION

1. Technical Field

The present invention relates to a method for treating a subject having a condition involving apoptosis. The present invention also relates to a method for inhibiting enhanced apoptosis.

2. Art Related

Apoptosis is a kind of genetically programmed cell death. Morphologically, apoptosis occurs along with the process as follows: condensation of the nucleus of the cell; cell shrinkage; cytoplasmic vacuolation and cell surface smoothing; enlargement of intercellular space; release of the cell from the pericellular region; fragmentation of the cell (to provide apoptosis body) and phagocytosis of the fragment by macrophage or the like. Biochemically, nucleosomal DNA is cleaved by endonuclease activity into 180–220 bp DNA fragments (Immunology Today 7: 115–119, 1986; Science 245:301–305, 1989, the cited references are herein incorporated by reference).

It has been revealed that apoptosis plays a role not only in physiological cell death concerning generation/differentiation and turnover of normal tissues and cells, but also in some diseases or conditions such as ischemic nerve cell death after cerebral infarction, cell death due to nuclear radiation or anti-cancer agent, cell death due to a toxin or virus infection, lymphocytopenia due to virus infection such as AIDS, photoreceptor cell death in light induced retinal photic injury, autoimmune disease, Alzheimer disease and inflammatory disease. Further, it is known that when an ocular surface receives a grave disorder due to some causes, apoptosis occurs on the ocular surface. For example, it is reported that apoptosis play a role in interstitial keratitis due to herpes simplex and corneal cell death after irradiation of ultraviolet (Klin Monatsbl Augenheilkd Vol. 217 No. 3: 178–182, 2000, Cornea Vol. 19 No. 1: 99–103, 2000, the cited references are herein incorporated by reference).

Accordingly, development of a new apoptosis controlling agent (i.e., apoptosis inhibitor or apoptosis inducer) which may provide a new type of drug with novel mode of action and be useful in a variety of fields including immune system, cerebral nerve system, optic nerve system, cancer and aging are desired.

Apoptosis can be induced by various kinds of stimulants including biological factors and ultraviolet irradiation. Despite of the stimulant, apoptosis process commonly includes cascade type activation of a group of proteolytic enzymes called as caspase family, which present in the cells. Namely, cell death inducing factor activates the cascade to activate caspases, especially caspase-3, and caspase-3 activates endonuclease fragmentizing DNA to cause apoptosis. Accordingly, the caspase activity, especially the caspase-3 activity can be used as an effective index of apoptosis.

Substances known to inhibit apoptosis include inhibitor of interleukin 1 converting enzyme, basic fibroblast growth factor (bFGF) and epidermal growth factor (EGF) (Japanese Patent Application Laid Open No. HEI.10-194988, the cited reference is herein incorporated by reference). Isocarbacyclin derivative has an inhibitory action on apoptosis of nerve cells and the like (U.S. Pat. No. 6,087,395, the cited reference is herein incorporated by reference), and prostaglandin E1 has an inhibitory action on daunorubicin-induced apoptosis of human leukemia cells (Japanese Journal of Inflammation Vol. 18, No. 5: 369–376, 1998, the cited reference is herein incorporated by reference).

Albumin is a protein that is widely present in animal/vegetable tissues and body fluids such as serum and lacrimal fluid. For example, human serum albumin is used for treating hypoalbuminemia, hemorrahagic shock and the like. In the ophthalmic field, it is also known to use albumin as a stabilizer in protein formulations such as fibronectin and interferon. The present inventor has previously proposed to use albumin for treatment of keratoconjuctival disorders or dry eye (U.S. Pat. No. 6,043,213, the cited reference is herein incorporated by reference). However, it is not known that albumin has an apoptosis inhibitory action.

SUMMARY OF THE INVENTION

An object of the present invention is to provide a method for treating a subject having a disease or condition involving apoptosis.

Another object of the present invention is to provide a method for inhibiting apoptosis. By inhibiting or suppressing enhanced apoptosis, various diseases or conditions associated with apoptosis are expected to be controlled.

The present inventors have conducted intensive studies on the biological activity of albumin and found that albumin exhibits an apoptosis inhibitory action, which has resulted in the completion of the present invention.

Namely, the present invention relates to a method for treating a subject having a disease or condition involving apoptosis, which comprises administration of an effective amount of albumin to the subject.

In another aspect, the present invention also relates to a method for inhibiting apoptosis, which comprises administering an effective amount of albumin to a subject having or being expected to have enhanced apoptosis.

The present inventors have also found that a cell growth factor and/or vitamin A used in combination with albumin will increase albumin's apoptosis inhibitory effect.

Accordingly, the present invention further relates to a method for treating a subject having a disease or condition involving apoptosis, which comprises administration of an effective amount of albumin and, a cell growth factor and/or vitamin A.

In another aspect, the present invention relates to a method for inhibiting apoptosis, which comprises administrating an effective amount of albumin, together with an effective amount of a cell growth factor and/or an effective amount of vitamin A to a subject having enhanced apoptosis.

DETAILED DESCRIPTION OF THE INVENTION

Figure 1:
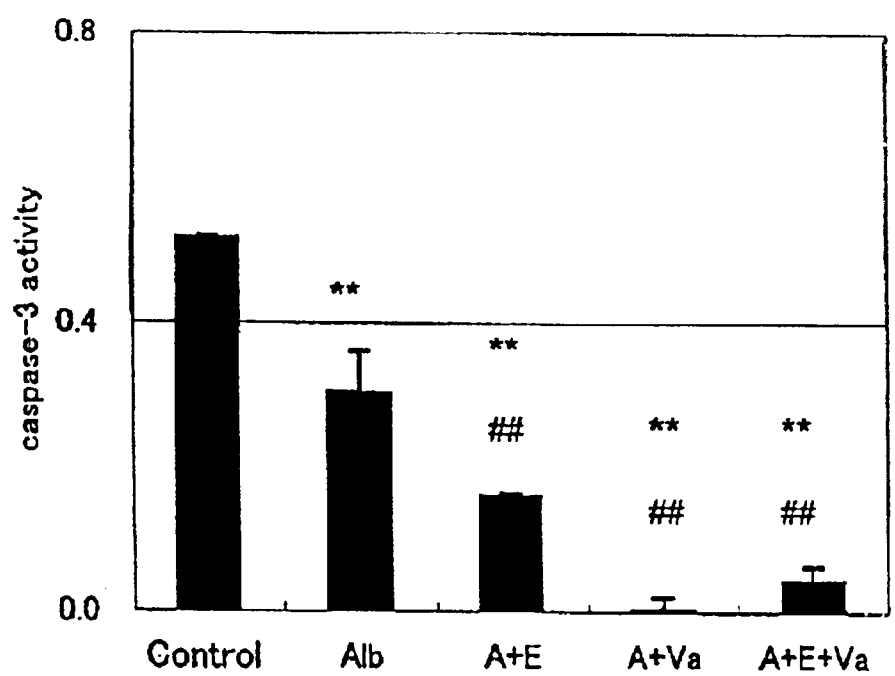
FIG. 1 represents the result of Example 2 demonstrating the effects of Albumin and Albumin+EGF and/or Vitamin A.

The origin of albumin used in the present invention is not particularly limited as long as its not antigenic. Human origin albumin such as human serum albumin may be preferably used. Especially, human serum albumin with the purity suitable for normal use in medical applications, such as a human serum albumin product containing not less than 80% of albumin when analyzed with electrophoresis, is especially preferable. In order to inactivate potentially contaminating viruses, those obtained by heat treatment are preferred. Special preference is given to commercially available medical-grade human serum albumin.

Gene recombinant albumin produced by transgenic microorganisms may also preferably be used in the present invention. The gene recombination technique is well known to those skilled in the art. Briefly explaining, a vector containing a gene coding a desired albumin (e.g., human albumin) may be prepared and introduced into a host cell to transform the cell. The transformed cell producing a desired protein may be selected. The selected transformed cell may be cultured and, from the cultured supernatant or cells, the desired albumin may be isolated and purified. Examples of the host cells include yeast and *Escherichia coli*, which are ordinarily used for producing a protein by those skilled in the art. In view of avoiding the risk of virus contamination in the composition, more preference is given to albumin as produced by the above gene recombination technique.

Cell growth factors used in the present invention may be any of the following: hepatocyte growth factor (HGF), epidermal growth factor (EGF), fibroblast growth factor (FGF), insulin-like growth factor (IGF), nerve growth factor (NGF), platelet-derived growth factor (PDGF), transforming growth factor (TGFα and TGFβ), keratinocyte growth factor (KGF) and a substance having these activities.

Especially preferable cell growth factors include epidermal growth factor, transforming growth factor, fibroblast growth factor, hepatocyte growth factor, insulin-like growth factor, platelet-derived growth factor and nerve growth factor.

The cell growth factors may be those naturally occurred substances which are produced in animals or animal cells or recombinant substances produced by means of conventional gene recombination techniques. Genetically modified cell growth factors having partially deleted, added or replaced amino acid sequence; or those having partially modified or deleted saccharide chains which are obtained by means of transgenic techniques may also be used as long as the modified products substantially exhibit similar action as of the naturally occurred products.

Vitamin A used in the present invention includes both vitamin A (retinol) and derivatives thereof. Vitamin A derivatives include, for example, vitamin A esters such as retinol palmitate and retinol acetate, all of which are preferably used. Additionally, any vitamin A derivatives having the same activity as that of vitamin A may be used in the present invention.

As used herein, the term "treatment", "treat" or "treating" refers to any means of control including prevention, care, relief of the condition, attenuation of the condition and arrest of progression.

According to the present invention the subject to be treated may be any mammalian subject including human and animals.

The present method may be effected by administering a pharmaceutical composition comprising an effective amount of albumin, or a composition comprising an effective amount of albumin together with an effective amount of a cell growth factor and/or vitamin A. According to the method, the composition may be applied systemically or topically to the subject. Especially, the composition is used in such routes as topical ocular administration, percutaneous administration, intravenous administration (including drip infusion) and subcutaneous administration. Topical ocular administration is especially preferable.

According to the present invention, the effective amount of albumin means an amount necessary for a desirable treatment. An optimum amount can be selected depending on the type of the subject such as animals or human, symptoms to be treated, age, sex, body weight, diet, other pharmaceuticals used in combination and various factors that are recognized by persons skilled in the art of the medical field. The effective amount also varies depending on the type or activity of albumin. The art in the medical field can determine the effective amount without undue experimentation.

When administrated topically to the eyes, the amount of albumin may typically be 0.01–100 $\mu$g/eye. Administration frequency may typically be 1–20 times, especially 1–10 times per day. In the systemic administration of 2 to 4 times per day or in a continuous administration, the amount of 0.001–500 mg/kg/day is normally sufficient to obtain a desirable apoptosis inhibiting effect.

According to the present method, a composition comprising an effective amount of albumin may be administrated to the subject. Examples of the dosage form of the composition used in the present invention include ophthalmic compositions such as eye solution, eye drops and eye ointment, injection and ointment, with preference given to the form suitable for topical ocular administration. Such formulations may be prepared in a conventional manner.

For example, in preparing the composition as eye drops, the composition may contain albumin in the amount of 0.0001 mg/ml–1000 mg/ml and a pharmaceutically acceptable diluent as desired.

The eye drops as above may be administered in the amount of about 1–1000 $\mu$l/eye, preferably about 10–50 $\mu$l/eye, more preferably about 30–50 $\mu$l/eye. Regarding the frequency of administration, it may be administrated about 1–20 times a day, especially 1–10 times a day. These amount and frequency of administration are only examples and are not intended to limit the scope of the present invention.

According to the present invention, when a cell growth factor and/or vitamin A are administrated in combination with albumin, the dose of the cell growth factor and/or vitamin A used may be suitably selected depending on the type of the subject such as animals or human, symptoms to be treated, age, sex, body weight, diet, other pharmaceuticals used in combination and various factors that are recognized by persons skilled in the art of the medical field. For example, in a typical eye drop preparation, the amount of cell growth factor may be about 0.0001–1000 $\mu$g/ml, preferably about 0.0005–100 $\mu$g/ml, more preferably about 0.001–10 $\mu$g/ml. The amount of vitamin A may be about 0.001–1000 $\mu$g/ml.

As used herein, the "pharmaceutically acceptable diluent" may be any diluent that is used for ophthalmic formulations known to persons skilled in the art. Examples of such diluents include water, physiological saline and artificial tear solution.

The composition used in the present invention may further comprise pharmaceutically acceptable additives. Examples of such additives include excipient, diluent, extender, solvent, lubricant, adjuvant, binder, disintegrator, coating agent, ointment base, emulsifier, dispersant, suspending agent, thickener, isotonizing agent, buffer, soothing agent, preservative, antioxidant, corrigent, flavor, colorant, functional agent (e.g., cyclodextrin and biodegrading polymer), stabilizer, pH modifier and chelating agent. The details of these additives may be obtained from general reference books on manufacturing pharmaceutical compositions.

Further, the composition may contain another pharmaceutically active ingredients as long as they are not contrary to the object of the present invention.

The subject to be treated by the present invention may be a subject having various diseases and conditions involving or being associated with apoptosis. The disease or condition may include, but not limited to, ischemic nerve cell death after cerebral infarction, carcinoma, autoimmune disease such as lymphopenia due to virus infection such as AIDS, Alzheimer's disease, inflammatory disease, ocular disorder by radiation of light (e.g., light induced retinal photic injury) and ocular surface disorder (e.g., cornea and conjunctiva).

The subject having or being expected to have enhanced apoptosis may include those actually suffered from enhanced apoptosis as well as those having or expected to have the above diseases or conditions.

The present invention will be explained in more detail with reference to the following examples, which are not intended to limit the scope of the present invention.

EXAMPLE 1

Method

Conjunctival epithelial cell line CCL-20.2 (obtained from American Type Culture Collection) was incubated in serum-containing medium 199 (Gibco) until 60–70% of confluent. The cells were washed with a serum-free medium and were resuspended in serum-free medium 199 containing albumin 1 mg/ml or serum-free medium 199 containing no albumin. The cells were then incubated for 24 hours and collected.

The caspase-3 activities of the collected cells were determined. The cells were lysed in a buffer solution (50 mM HEPES, 1 mM dithiothreitol and 0.1 mM EDTA (pH7.4)) containing 0.1% CHAPS (3-[(3-cholamidopropyl) dimethylammonio]-2-hydroxy-1-propanesulfonic acid) and were centrifuged to collect the supernatant. The caspase activity in the supernatant was determined with 0.1 mM fluorescence substrate (Z-DEVD-AFC) by means of fluorescence intensity measurement(em:505 nm, ex:400 nm) (n=4).

DNA fragmentation was determined with the Cell Death Detection ELISAPLUS (Roche Diagnostics Corporation, Basel, Switzerland). $2 \times 10^4$ cells were lysed with 0.1 ml of buffering solution and centrifuged to collect the supernatant. The obtained supernatant as well as positive and background controls, each in the amount of 20 μl, was respectively added to a plate coated with streptavidin. After adding an immunologic reagent (incubation buffer: antihistone-biotin: anti-DNA-POD=18:1:1) 80 μl to each plate, it was coated with a film and shaken at 300 rpm for 2 hours at room temperature. Then the plate was washed with incubation buffer 250–300 μl for 3 times. After adding substrate (ABTS) solution 100 μl to the plate, it was shaken at 250 rpm for 10–20 minutes at room temperature. The measurement was 405 nm (reference wavelength 492 nm)(n=4).

Result

Table 1 shows the caspase-3 activity. The lower the caspase-3 activity, the more apoptosis was inhibited. Table 2 shows the DNA fragmentation.

TABLE 1

Caspase-3 activity

|  | Caspase-3 activity (n mol/hr/mg protein) mean ± S.E. |
| --- | --- |
| Control group (without albumin) | 0.744 ± 0.246 |
| Test group (with albumin) | 0.510 ± 0.191 |

TABLE 2

DNA fragmentation

|  | DNA fragmentation mean ± S.E. |
| --- | --- |
| Control group (without albumin) | 0.111 ± 0.018 |
| Test group (with albumin) | 0.096 ± 0.047 |

The caspase-3 activity and DNA fragmentation of the test group were both lower than those of the control group. In other words, the results shown in Tables 1 and 2 demonstrate the correlation between the caspase-3 activity, which is considered to be an index of apoptosis, and the DNA fragmentation, which represents the actual occurrence of apoptosis.

These results revealed that albumin inhibited apoptosis.

EXAMPLE 2

Method

Conjunctival epithelial cell line CCL-20.2 (obtained from American Type Culture Collection) was incubated in serum-containing medium 199 (Gibco) until 70–80% of confluent. The cells were washed with serum-free medium and resuspended in serum-free medium 199 containing albumin 3 mg/ml; albumin 3 mg/ml+EGF10 ng/ml; albumin 3 mg/ml+ vitamin A 0.1 μg/ml; or albumin 3 mg/ml+EGF10 ng/ml+ vitamin A 0.1 μg/ml. The control group was resuspended in serum-free medium 199 containing none of these ingredients. The cells were incubated for 24 hours and collected.

The caspase-3 activities of the collected cells were measured. The cells were lysed in a buffer solution (50 mM HEPES, 1 mM dithiothreitol and 0.1 mM EDTA (pH7.4)) containing 0.1% CHAPS (3-[(3-cholamidopropyl) dimethylammonio]-2-hydroxy-1-propanesulfonic acid) and centrifuged to collect the supernatant. The caspase activity in the supernatant was determined with 0.1 mM fluorescence substrate (Z-DEVD-AFC) by means of fluorescence intensity measurement(em:505 nm, ex:400 nm) (n=3).

Result

Results are shown in FIG. 1. The lower the caspase-3 activity, the more apoptosis was inhibited.

The caspase-3 activities of the test groups (albumin, albumin+EGF (A+E), albumin+vitamin A (A+Va) and albumin+EGF+vitamin A (A+E+Va)) were significantly lower than that of the control group.

Compared with the group using only albumin, the caspase-3 activity of groups using combined ingredients (albumin+EGF, albumin+vitamin A and albumin+EGF+ vitamin A) were significantly low.

EXAMPLE 3

Method

Conjunctival epithelial cell line CCL-20.2 (obtained from American Type Culture Collection) was incubated in serum-containing medium 199 (Gibco) until 70–80% of confluent.

The cells were washed with serum-free medium and then resuspended in serum-free medium 199 containing albumin 1 mg/ml, albumin 1 mg/ml+TGFα10 ng/ml, or albumin 1 mg/ml+TGFβ10 ng/ml. The control group was resuspended in serum-free medium 199 containing none of these ingredients. The cells were incubated for 24 hours and collected.

The caspase-3 activities of the collected cells were measured. The cells were lysed in a buffer solution (50 mM HEPES, 1 mM dithiothreitol and 0.1 mM EDTA (pH7.4)) containing 0.1% CHAPS (3-[(3-cholamidopropyl) dimethylammonio]-2-hydroxy-1-propanesulfonic acid) and centrifuged to collect the supernatant. The caspase activity in the supernatant was determined with 0.1 mM fluorescence substrate (Z-DEVD-AFC) by means of fluorescence intensity measurement (em:505 nm, ex:400 nm) (n=3). Results are shown in FIG. 2.

Figure 2:
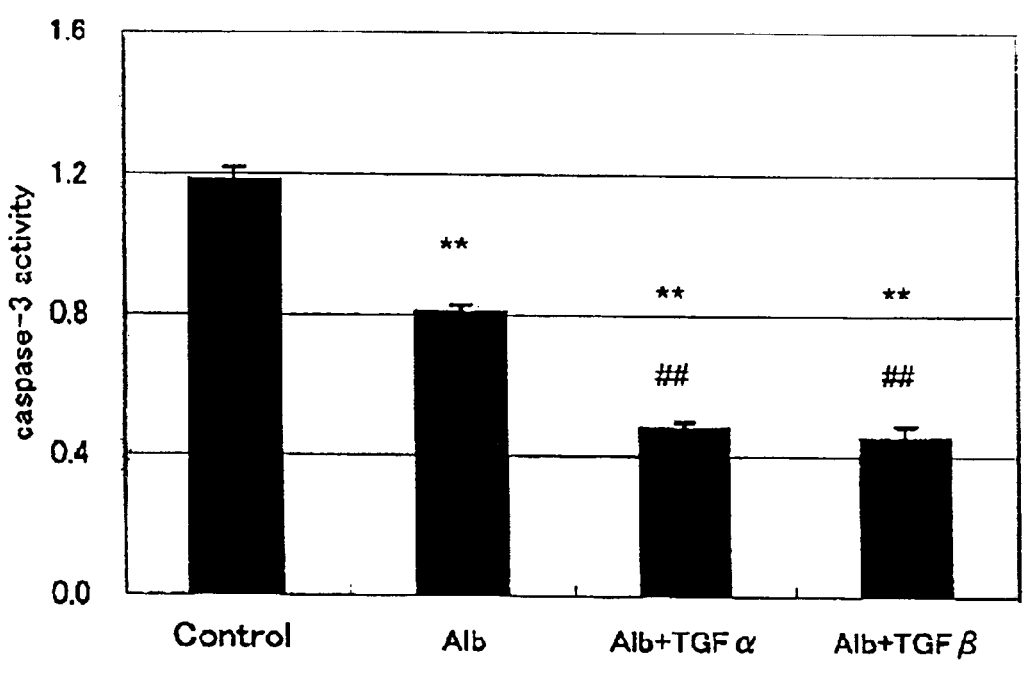
FIG. 2 represents the result of Example 3, demonstrating the effects of Albumin and Albumin+TGFα as well as Albumin+TGFβ

FIG. 2 shows the caspase-3 activity. The lower the caspase-3 activity, the more apoptosis was inhibited.

The caspase-3 activity of the test groups (albumin, albumin+TGFα and albumin+TGFβ) were significantly lower than that of the control group.

Compared with the group using only albumin, the caspase-3 activity of the groups using combined ingredients (albumin+TGFα and albumin+TGFβ) was significantly low.

EXAMPLE 4

Method

Conjunctival epithelial cell line CCL-20.2 (obtained from American Type Culture Collection) was incubated in serum-containing medium 199 (Gibco) until 70–80% of confluent. The cells were washed with serum-free medium and then resuspended in serum-free medium 199 containing albumin 1 mg/ml, albumin 1 mg/ml+bFGF 5 ng/ml, albumin 1 mg/ml+HGF 50 ng/ml, albumin 1 mg/ml+IGF 10 ng/ml, albumin 1 mg/ml+PDGF 10 ng/ml, or albumin 1 mg/ml+ NGF 50 ng/ml. The cells were incubated for 24 hours and collected.

The caspase-3 activities of the collected cells were measured. The cells were lysed in a buffer solution (50 mM HEPES, 1 mM dithiothreitol and 0.1 mM EDTA (pH7.4)) containing 0.1% CHAPS (3-[(3-cholamidopropyl) dimethylammonio]-2-hydroxy-1-propanesulfonic acid) and centrifuged to collect the supernatant. The caspase activity in the supernatant was determined with 0.1 mM fluorescence substrate (Z-DEVD-AFC) by means of fluorescence intensity measurement (em: 505 nm, ex: 400 nm) (n=3). Results are shown in FIGS. 3, 4 and 5.

Results

Figure 3:
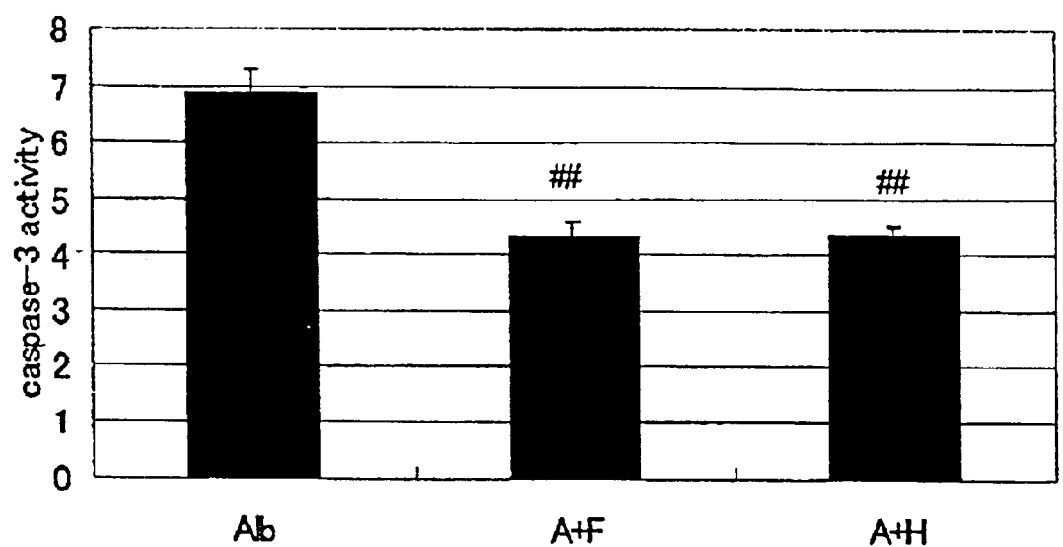
FIG. 3 represents the result of Example 4, demonstrating the synergic effects of Albumin+bFGF and Albumin+HGF.
Figure 4:
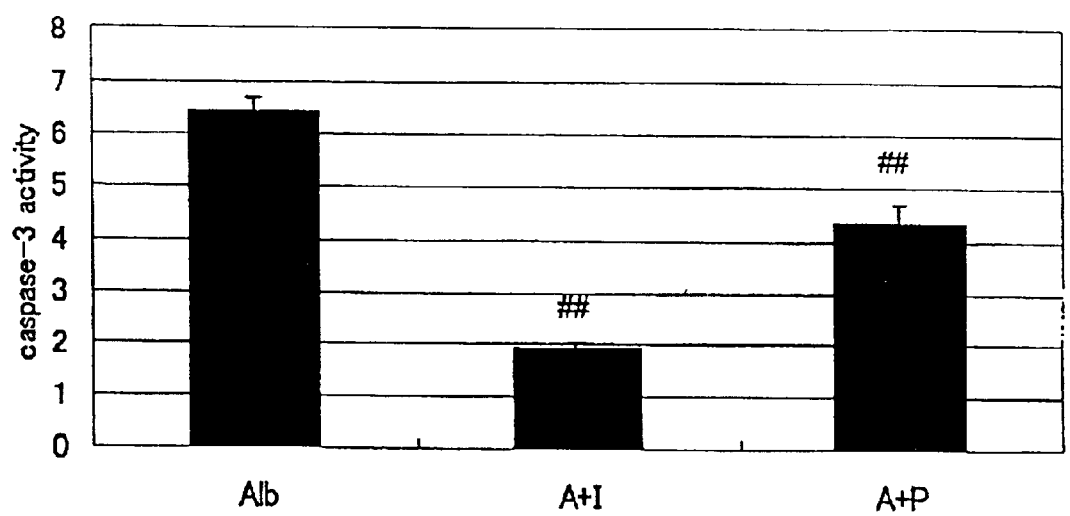
FIG. 4 represents the result of Example 4, demonstrating the synergic effects of Albumin+IGF and Albumin+PDGF.
Figure 5:
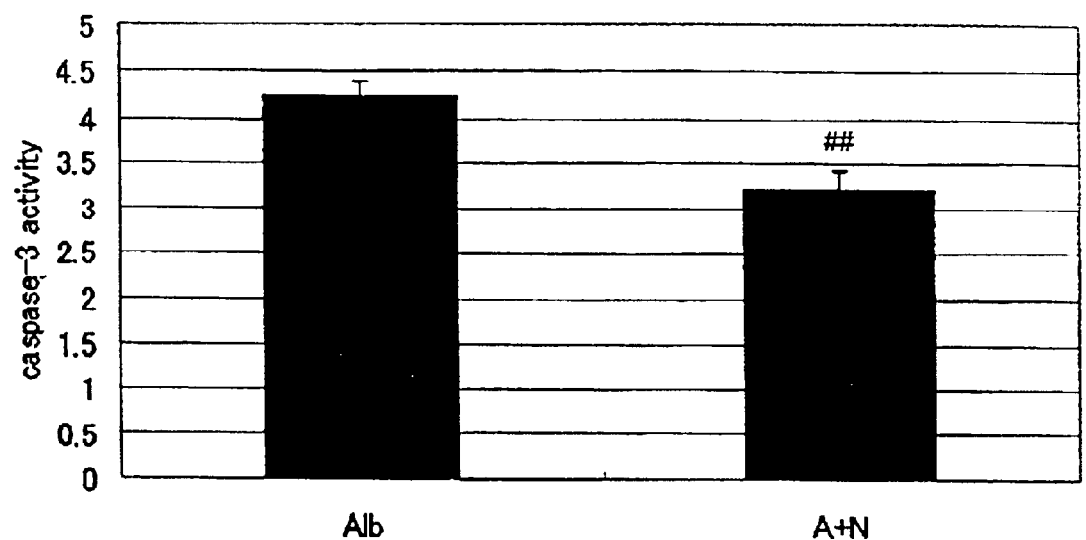
FIG. 5 represents the result of Example 4, demonstrating the synergic effect of Albumin+NGF.

FIGS. 3, 4 and 5 show the caspase-3 activity. The lower the caspase-3 activity, the more apoptosis was inhibited.

Compared with the group using only albumin, the caspase-3 activities of the groups using combined ingredients (albumin+bFGF (A+F), albumin+HGF (A+H), albumin+IGF (A+I), albumin+PDGF (A+P) and albumin+ NGF (A+N)) were significantly low.

These results indicate that albumin has an apoptosis inhibitory action, and albumin's apoptosis inhibitory activity can be increased when it is used in combination with a cell growth factor and/or vitamin A.

What is claimed is:

1. A method for treating a subject having an ocular surface disorder involving apoptosis, which comprises administering albumin topically to an eye of a subject in need thereof in an amount effective to treat said ocular surface disorder.

2. The method of claim 1, wherein albumin is human origin albumin.

3. The method of claim 1, wherein albumin is a gene recombinant albumin.

4. The method of claim 1, which comprises administrating an effective amount of albumin, together with an effective amount of cell growth factor and/or an effective amount of vitamin A to the subject.

5. The method of claim 4, wherein the cell growth factor is selected from the group consisting of epidermal growth factor, transforming growth factor, fibroblast growth factor, hepatocyte growth factor, insulin-like growth factor, platelet-derived growth factor and nerve growth factor.

6. The method of claim 4, wherein albumin is human origin albumin.

7. The method of claim 4, wherein albumin is a gene recombinant albumin.

8. The method of claim 4, wherein albumin and cell growth factor and/or vitamin A are administrated topically to the eyes.

9. A method for inhibiting an ocular surface disorder involving apoptosis, which comprises administering albumin topically to an eye of a subject in need thereof in an amount effective to inhibit said ocular surface disorder.

10. The method of claim 9, wherein albumin is human origin albumin.

11. The method of claim 9, wherein albumin is a gene-recombinant albumin.

12. The method of claim 9, which comprises administrating an effective amount of albumin, together with an effective amount of cell growth factor and/or an effective amount of vitamin A to the subject.

13. The method of claim 12, wherein the cell growth factor is selected from the group consisting of epidermal growth factor, transforming growth factor, fibroblast growth factor, hepatocyte growth factor, insulin-like growth factor, platelet-derived growth factor and nerve growth factor.

14. The method of claim 12, wherein albumin is human origin albumin.

15. The method of claim 12, wherein albumin is a gene recombinant albumin.

16. The method of claim 12, wherein albumin and the cell growth factor and/or vitamin A are administered topically to the eyes.

* * * * *